United States Patent [19]

Lin et al.

[11] Patent Number: 4,828,671
[45] Date of Patent: May 9, 1989

[54] UNITARY SELF-REFERENCING COMBINED DUAL GAS SENSOR

[75] Inventors: Ching-Yu Lin, Monroeville, Pa.; William H. McIntyre, Orrville, Ohio

[73] Assignee: Westinghouse Electric Corp., Pittsburgh, Pa.

[21] Appl. No.: 175,433

[22] Filed: Mar. 30, 1988

[51] Int. Cl.[4] ............................................. G01N 27/46
[52] U.S. Cl. .................................... 204/412; 204/424; 204/427
[58] Field of Search ................... 204/15, 412, 421-429

[56]  References Cited
U.S. PATENT DOCUMENTS

| | | | |
|---|---|---|---|
| 3,915,830 | 10/1975 | Isenberg | 204/426 |
| 4,295,939 | 10/1981 | Poirier et al. | 204/15 |
| 4,306,957 | 12/1981 | Ishitani et al. | 204/425 |
| 4,377,460 | 3/1983 | Hirayama et al. | 204/15 |
| 4,388,155 | 6/1983 | Chamberland et al. | 204/427 |
| 4,391,690 | 7/1983 | Lin et al. | 204/428 |
| 4,394,240 | 7/1983 | Pebler | 204/412 |
| 4,399,017 | 8/1983 | Inoue et al. | 204/425 |
| 4,427,525 | 1/1984 | Lin et al. | 204/427 |
| 4,622,105 | 11/1986 | Liu et al | 204/424 |

Primary Examiner—T. Tung
Attorney, Agent, or Firm—Daniel P. Cillo

[57]  ABSTRACT

A solid electrolyte dual gas sensor 10 is made, containing a container body of a first solid electrolyte 11, in contact with a monitor electrode 17 exposed to a monitored gas environment 13 containing selected gas components to be measured, and in contact with a reference electrode 15 which is additionally isolated from the monitored gas environment by a second solid electrolyte 16, and optionally 14, where the second solid electrolyte, at the operating temperature of the gas sensor, is effective to dissociate to provide the sole source of self-generated gases at the reference electrode 15, corresponding to the selected gas components to be measured in the monitored gas environment, where, at the operating temperature of the sensor, the first solid electrolyte 11 is effective to conduct oxygen ions, and the second solid electrolyte 16 is effective to conduct ions selected from the group of sodium ions, potassium ions, and their mixtures.

13 Claims, 3 Drawing Sheets

UNITARY SELF-REFERENCING COMBINED DUAL GAS SENSOR

BACKGROUND OF THE INVENTION

1. Field of the Invention

This invention relates to unitary, self-generating reference gas sensors, useful to monitor not only a $SO_2$, $CO_2$ or $NO_2$ component, but also an $O_2$ gas component of a monitored gas environment.

2. Description of the Prior Art

The requirements for monitoring and controlling stack gas pollutants have resulted in the development of solid electrolyte gas sensors having electrolyte compositions uniquely responsive to gases such as $SO_2$, $CO_2$ and $NO_2$. These sensors are electrochemical concentration cells which sense the equilibrium of a gas species of interest and generate an EMF signal corresponding to the difference in partial pressure of the gas species across the solid electrolyte sensor. Typically, the solid state sensor includes an ion conductive solid electrolyte with electrodes disposed on its opposite surfaces. The stack gas, or monitored gas stream, contacts a sensing electrode, while the opposite electrode serves as a reference electrode which is contacted with a reference gas stream. Conventional solid electrolyte compositions require operating temperatures of between 200° C. and 900° C. to exhibit the desired ion conductivity to generate a suitable EMF signal.

In the past, a major problem with these devices was isolation of the monitored gas from the reference gas, to prevent unpredictable drift in the measurement signal. Hirayama et. al., in U.S. Pat. No. 4,377,460, solved this sealing problem by using a closed end, gas impermeable, mullite ($3Al_2O_3 \cdot 2SiO_2$) tube, which acts as an alkali ion conductive membrane at high temperatures. The mullite tube, like most ceramics, incorporates some alkali oxide impurities, such as $K_2O$, making it a $K^+$ ionic conductor at high temperatures. This tube was used to separate the two gas streams and provide two identical alkali ion conductive half cells secured to opposite sides of the mullite.

The two, alkali ion conductive solid electrolyte discs used in each half cell of the Hirayama et al. design, to monitor $SO_2$, $CO_2$ or $NO_2$, were made of $K_2SO_4$, $Na_2CO_3$, or $NaNO_3$ respectively. A platinum electrode was attached to one side of each half cell electrode. In the case of a $SO_2+O_2$ reference gas stream, this provided the cell assembly:

$SO_2+O_2$ Reference Gas,
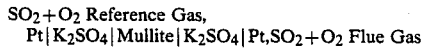

Lin et al., in U.S. Pat. No. 4,427,525, taught a somewhat similar system, but used calcia stabilized zirconia as the tube membrane. This tube membrane is oxygen ion permeable. A separate cell which can be used to measure the partial pressure of $O_2$ is disposed across this tube, removed a distance from the two half cells used to monitor $SO_2$, $CO_2$ or $NO_2$, with common circuitry connecting all the cells, making it a dual gas sensing apparatus.

In an attempt to not only effectively seal monitored gas from the reference gas, but to also eliminate the effect of $O_2$ on the EMF signal measurement of $SO_2$, Lin et al., in U.S. Pat. No. 4,391,690, constructed a dual gas monitoring sensor device. Different and separate sensor cells are described: an $SO_2$ cell having a $K_2SO_4$ solid electrolyte, which is fed a $SO_2$ reference gas stream, and is also connected to a source of $O_2$; and an $O_2$ cell having an oxygen ion conductive solid electrolyte, which is fed an air reference gas stream.

In the Lin et al. patent, each of the two different and separate cells have their own EMF measuring electrical circuit, to separately monitor the $O_2$ partial pressure and the $SO_2$ concentration of the monitored gas environment. If the $O_2$ concentration of the monitored gas environment is shown to change by the $O_2$ cell circuitry, the source of $O_2$ connected to the $SO_2$ cell could be turned on or adjusted, to establish a correct $O_2$ balance at the $SO_2$ cell electrodes. Another embodiment utilizes $MgSO_4$ as a decomposable reference source of gas for the $SO_2$ cell. These sensor designs, however, are complicated to make and operate. Also, the use of a $SO_2+O_2$ reference gas stream, where required, is inconvenient and expensive, since a constant supply of certified tank gas is needed.

Several instances of simplified, unitary gas sensors have been disclosed in the art. Isenberg, in U.S. Pat. No. 3,915,830, relating to $O_2$ sensors, taught hermetically encapsulating a metal/metal oxide reference medium, such as nickel/nickel oxide, exhibiting a stable oxygen activity, within a small, stabilized zirconia solid electrolyte disc. A metal electrode is attached to the outside of the solid electrolyte and is in electronic communication with the encapsulated reference medium. Sealing other reference media, such as oxygen gas or air within the solid electrolyte is also mentioned. Inoue et al., in U.S. Pat. No. 4,399,017, taught encapsulation of an electrode within a microporous, stabilized zirconia solid electrolyte. A second electrode is attached to the outside of the solid electrolyte, and the whole covered with porous ceramic. Upon application of a DC current, migration of oxygen ions, and diffusion of oxygen gas through the microporous solid electrolyte, can establish a reference partial pressure of oxygen at the interface between the microporous solid electrolyte and the encapsulated electrode, to enable measurement of oxygen gas content in flue gas.

Pebler, in U.S. Pat. No. 4,394,240, taught triangular, combination, multisensor electrochemical cells, which form an internal cavity which contains a common internal gas forming reference. In the triangular configuration, two sides are made of stabilized zirconia, oxygen ion conductive solid electrolyte and measure partial pressure of $O_2$, and the third side can be made of $K_2SO_4$ solid electrolyte when the partial pressure of $SO_3$ or $SO_2$ gases are to be measured. Reference electrodes are disposed on the inside electrolyte walls of the triangular configuration and sensing electrodes are disposed on the outside electrolyte walls.

The measuring concept in Pebler utilizes heating a central, enclosed, $MgSO_4$, $MnSO_4$ or $Ag_2SO_4$ reference material, which provides $SO_3$ on decomposition. This reference material must be kept sealed from $K_2SO_4$ electrolyte, because of the possible reaction of these two components at high temperatures. Each of the three cells has its own circuitry. Two cells are exposed to flue gas, and one of the zirconia cells is exposed to an environment of known oxygen partial pressure, such as air. In a somewhat similar concept, involving two contacting electrolyte portions of two different gas monitors, Poirier et al., in U.S. Pat. No. 4,295,939, teach use of a reference medium, such as $MgSO_4$ plus $MgO$, which upon application of heat provides a metal oxide plus $SO_2$ within a cavity adjacent to $K_2SO_4$ solid electrolyte of one cell, and use of a metal/metal oxide reference medium in a cavity of a second cell enclosed in a stabilized zirconia solid electrolyte.

None of these designs provide a simple, inexpensive construction that would be effective to measure $SO_2$, $CO_2$ or $NO_2$ content of flue gases. Lin et al., in U.S. Ser. No. 175,434, filed on Mar. 30, 1988, (W.E. Case No. 53,216), teach a simplified, inexpensive, unitary, self-generating reference gas sensor. There, a reference electrode is isolated from the monitored gas environment by solid electrolyte, and the solid electrolyte itself, upon the application of heat, is effective to dissociate and provide the sole source of a self-generated gas, such as $SO_2+O_2$, $CO_2+O_2$, or $NO_2+O_2$ at the reference electrode. That design could measure only $SO_2+O_2$, $CO_2+O_2$, or $NO_2+O_2$, so that a separate $O_2$ sensor would have to be installed along with the Lin et al. sensor, and the $O_2$ concentration, in terms of voltage output, would have to be compensated for electronically. What is needed is a further advanced design. It is an object of this invention to provide such a construction.

SUMMARY OF THE INVENTION

Accordingly, the invention resides in a solid electrolyte dual gas sensor apparatus for measuring two selected component gases of a monitored gas environment, by generating electrical signals on the basis of a difference in the partial pressure between the two selected component gases of the monitored gas environment, at first and second monitor electrode means in contact with the monitored gas environment and solid electrolyte, and the corresponding component reference gases, at reference electrode means in contact with the reference gas environment and solid electrolyte; characterized in that the reference electrode means contacts a first and a second solid electrolyte surface, where, at the operating temperature of the sensor, the first electrolyte is oxygen ion conductive, and the second electrolyte conducts ions selected from the group consisting of sodium ions, potassium ions and their mixtures, which second electrolyte itself is a self-reference electrolyte, which upon the application of heat, is effective to dissociate to provide the sole source of constant partial pressures of self-generated gases, at the reference electrode means, the generated gases corresponding to the selected component gases to be measured. The first electrolyte preferably acts as a containment vessel for a majority of the second electrolyte.

The invention is further characterized in that the second electrolyte can be composed of a void free section at least 95% dense, pressed into contact with the reference electrode, and a void free section, at least 95% dense, which contacts the monitored gas environment and supports a metal monitor electrode. This latter section can overlap the edges of the first electrolyte container, to ensure that there is no gas leakage to the interior reference electrode which is in contact with the reference gas environment. Monitor electrode means contact the outer surface of both electrolytes. This provides a unitary, dual gas sensor apparatus, where the combination of solid electrolytes is effective to prevent monitored gas contact with the reference electrode means and to provide an enclosure for the reference electrode means.

Also included are measuring circuit means connected to all the electrodes of the sensor, which is effective to generate electrical signals to measure the selected gas components in the monitored gas environment. When the selected gas component to be monitored is $SO_2$, the second electrolyte will be selected from $K_2SO_4$ and $Na_2SO_4$. When the selected gas component to be monitored is $CO_2$ or the like gases, the self-reference second electrolyte will be selected from $K_2CO_3$ and $Na_2CO_3$. When the selected gas component to be monitored is $NO_2$, the self-reference second electrolyte will be selected from $KNO_3$ and $NaNO_3$. The first electrolyte will preferably be made of stabilized zirconia. The preferred electrodes are platinum. In the case of $KNO_3$ or $NaNO_3$ self-reference electrodes, which have low melting points, requiring the sensor to operate at low temperatures, i.e., at approximately 200° C. to 300° C., the first electrolyte must be thin, so that oxygen ion conductivity will be sufficient to generate an electrical signal.

Thus, there is no need to supply any separate reference gas stream in the reference system. Additionally, this dual gas sensor can be miniaturized, and its manufacture and operation can provide substantial cost savings. This sensor is effective within the temperature range of 200° C. to 900° C.

BRIEF DESCRIPTION OF THE DRAWINGS

In order that the invention can be more clearly understood, convenient embodiments thereof will now be described, by way of example, with reference to the accompanying drawings in which.

DESCRIPTION OF THE PREFERRED EMBODIMENTS

Figure 1:
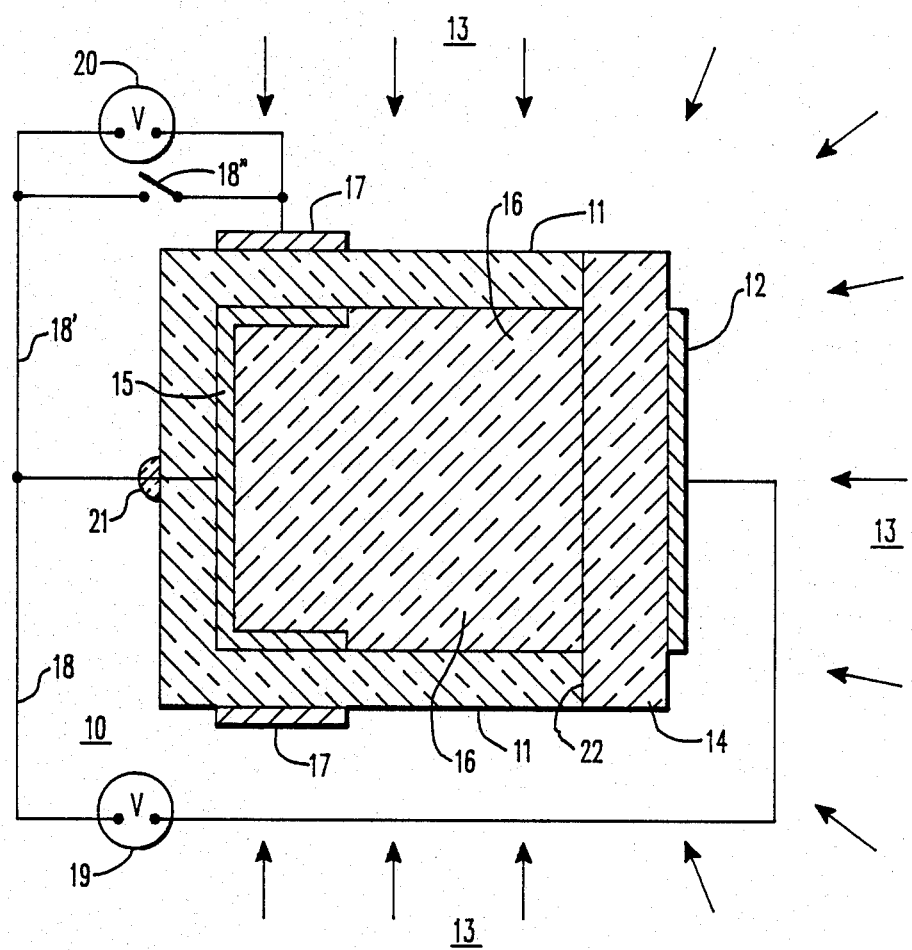
FIG. 1 is a cross-sectional view of one embodiment of a unitary, self-generating reference gas, dual sensor of this invention.

Referring now to FIG. 1, solid electrolyte, unitary, dual gas sensor electrochemical cell 10 is shown. This dual gas sensor cell is preferably contained within a non-porous, high temperature stable, gas impermeable vessel 11. This vessel is usually a dense ceramic cylindrical cup or bored out tube made of a material that conducts oxygen ions at relatively high temperatures, such as stabilized zirconia, which acts as a first solid electrolyte for the sensor. The preferred first electrolyte 11 is stabilized zirconia, preferably $ZrO_2$ doped with a minor amount, usually from 5 atom percent to 15 atom percent, of yttrium oxide, $Y_2O_3$. Calcia, CaO, can also be used as a dopant. This solid electrolyte container or vessel 11 would be isostatically pressed at high temperatures, to provide a sintered, high density (at least 90% dense) cup or tube.

A first, metal, monitor electrode means 12, is in contact with the monitored gas environment 13, shown by arrows, containing the gas components to be measure, and a void-free, second solid oxide electrolyte for the sensor. The second solid electrolyte can be divided into highly densified section 14, which contacts the metal, monitor electrode means 12, and sintered, pressed section 16 which contacts the metal, reference electrode means 15 of the sensor. This reference electrode is preferably a single, common, electrode structure. The second electrolyte sections 14 and 16 would both be made of a material which, at high temperatures, is effective to conduct ions selected from one of the group consisting of sodium ions and potassium ions. Sections 14 and 16 would both be made of the same material. Preferably, electrolyte section 16 is usually pressed into place within electrolyte container 11 and can be densified to over about 98% of theoretical density. Electrolyte body 14 is a single member, such as a disc, that can be isostatically pressed at high temperature and pressure to over 98% of theoretical density.

In the preferred embodiment, electrolyte section 16, when initially formed, extends somewhat beyond the vessel top, so that when electrolyte section 14 is pressed against section 16 a good contact is established and ionic conductivity is not hindered at the interface of the two. Also, electrolyte section 16 overlaps the edges of the first electrolyte containment vessel 11 at 22, to insure that there is no gas leakage of monitored gas environment 13 to the interior reference electrode 15. Second, metal, monitor electrode means 17 is on the outside of electrolyte vessel 11, preferably as a continuous band of wire. Thus, both monitor electrodes 13 and 17 contact the monitored gas environment 13. First monitor electrode 12 also contacts electrolyte body 14, and second monitor electrode 17 also contacts electrolyte body 11 in the form of a containing vessel. Also, as shown, the electrolytes contact the monitored gas environment.

The pressed, solid electrolyte sections 14 and 16 will preferably be at least 95% dense, and will be of at least 95% purity. The solid electrolyte 11, 14 and 16 will be made from sintered, submicron particles, preferably in a range from approximately 0.5 micron to 0.9 micron, and will be effective to prevent monitored gas 13 contact with the reference electrode means 15. The preferred material for electrodes 12, 15 and 17, as well as electrical leads 18, is platinum.

Measuring circuit means, comprising electrical lead wires 18 and 18' are connected to the electrode means 12 and 15, and 15 and 17 respectively, to establish two circuits. The circuit means are also connected to voltmeters 19 and 20 as shown. These circuits respond to electrical signals generated in the sensor. These circuits provide an indication of both the partial pressures of selected gas components in the monitored gas environment to be measured, and the partial pressures of the corresponding similar gases generated by decomposition of the second electrolyte bodies 16 and 14, as described hereinafter.

A high temperature stable, ceramic oxide sealant 21, such as, for example, a mixture of 49 mole % $La_2O_3$ and 51 mole % $AL_2O_3$, having a melting point of approximately 1710° C., can be used to ensure isolation of monitor electrode means 15. A spring means, not shown, can be used to insure good electronic contact between bodies 14 and 16. The main body of this dual gas sensor can be inserted or assembled into a probe structure, having a heating element and temperature control, to provide a gas-sensing apparatus.

The EMF (electromotive force) signals generated by the solid electrolyte dual gas sensor cell, are developed in accordance with the well-known Nernst equation, where the variables include the cell temperature, and the variation of partial pressure of the gas components of interest in the monitored gas environment at the monitor electrodes 12 and 17, and the partial pressure of the same reference gases at the common reference electrode 15. In this invention, the solid second electrolyte itself is a self-reference electrolyte, which upon the application of heat, is effective to dissociate to provide the sole source of reference gases.

In the case where the monitored gas environment contains $SO_2$ and $O_2$, two gas components to be measured, and where the solid electrolytes are $K_2SO_4$, 14 and 16 for the $SO_2$ cell portion of the sensor, and stabilized zirconia, 11, for the $O_2$ cell portion of the sensor, upon operation of the sensor cell at from 600° C. to 900° C., the $K_2SO_4$ solid electrolyte will be in equilibrium dissociation to provide a $SO_2+O_2$ reference gas, according to the chemical reaction:

$$K_2SO_4 \rightleftharpoons 2K^+ + SO_2 + O_2.$$

The cell assemblies will be:

$SO_2+O_2$ Reference Gas, $Pt|K_2SO_4|Pt$, $SO_2+O_2$ Flue gas, and $SO_2+O_2$ Reference Gas, $Pt|ZrO_2 \cdot Y_2O_3|Pt$, $SO_2+O_2$ Flue gas.

In this case, the EMF would be calculated from the equation:

$$EMF = \frac{RT}{2F} \ln \frac{P_{SO_2} \cdot P_{O_2}}{P'_{SO_2} \cdot P'_{O_2}}, \text{ for the } SO_2 \text{ cell, and}$$

$$EMF = \frac{RT}{4F} \ln \frac{P_{O_2}}{P'_{O_2}}, \text{ for the } O_2 \text{ cell,}$$

where R=the universal gas constant, T=temperature °K., F=Faraday Constant (23,061 cal./volt), P=partial pressure of reference gas, and P'=partial pressure of monitored gas, where R, T, F, and P are known. In the $SO_2$ cell, there are two electrons transferring and for the $O_2$ cell, there are four electrons transferring. From these equations, a direct measurement of $SO_2$ and $O_2$ component gases in the monitored gas environment can be made by the measurement of the EMF of the sensor cells.

Since the zirconia cell and the $K_2SO_4$ cell share a common inner reference electrode 15, the sensor is not only able to monitor $SO_2$ and $O_2$ separately, but also is capable of monitoring $SO_2$ directly in the flue gas independent of $O_2$ levels by shorting the sensing and reference electrodes of the zirconia cell; this provides an equal $O_2$ potential between the inner electrode and ambient.

For example, on open circuit, as shown in FIG. 1, voltmeter 19 will read: $SO_2$ concentration in terms of mV. + $O_2$ concentration in terms of mV., at an approximately 100 mV./decade concentration slope (slope of the calibration curve for $SO_2+O_2$). Voltmeter 20 will read $O_2$ concentration in terms of mV., at approximately 54 mV./decade concentration slope (slope of the calibration curve for $O_2$ alone). To get the concentration of $SO_2$ from a calibration curve, the following equation is used:

$EMF_{SO_2} = [(EMF_{SO_2} + EMF_{O_2})$ from voltmeter 19] $- [2EMF_{O_2}$ from voltmeter 20]

The ppm. $SO_2$ concentration is then read from the calibration curve, knowing $EMF_{SO_2}$. If the circuit 18' is shorted, for example switch 18" is thrown to close the circuit, the oxygen concentration across the first electrolyte 11 will equalize, providing an equal oxygen potential between the inner electrode and ambient. This is caused because $O_2$ will be pumped from the monitored gas environment, converted to oxygen ions, and then back to $O_2$ within the $K_2SO_4$ electrolyte. In this case, voltmeter 19 will read $EMF_{SO_2}$ alone, since $EMF_{O_2}=0$, by the equation:

$$EMF_{SO_2} = [EMF_{SO_2+O}] - [O].$$

When the selected gas component to be monitored is $SO_2$, the second solid electrolyte 14 and 16 will be selected from $K_2SO_4$ and $Na_2SO_4$. At 600° C. to 900° C. sensor operation, solid $K_2SO_4$ will be in equilibrium dissociation with $2K^+ + SO_2 + O_2$. At 600° C. to 780° C. sensor operation, solid $Na_2SO_4$ will be in equilibrium dissociation with $2Na^+ + SO_2 + O_2$. When the selected gas component to be monitored is $CO_2$, the solid electrolyte 14 and 16 will be selected from $K_2CO_3$ and $Na_2CO_3$. At 600° C. to 780° C. sensor operation solid $K_2CO_3$ will be in equilibrium dissociation with $2K^+ + CO_2 + \frac{1}{2}O_2$ and solid $Na_2CO_3$ will be in equilibrium dissociation with $2Na^+ + CO_2 + \frac{1}{2}O_2$. When the selected gas component to be monitored is $NO_2$, the solid electrolyte 14 and 16 will be selected from $KNO_3$ and $NaNO_3$. At 200° C. to 300° C. sensor operation, solid $KNO_3$ will be in equilibrium dissociation with $K^+ + NO_2 + \frac{1}{2}O_2$ and solid $NaNO_3$ will be in equilibrium dissociation with $Na^+ + NO_2 + \frac{1}{2}O_2$. This last sensor can be operated only at low or cooled flue gas temperatures, and must utilize a thin wall first electrolyte structure 11.

In all instances, at the operating temperature of the sensor cell, the self-reference second solid electrolyte, 14 and 16, itself provides the sole source of $O_2^+$, $SO_2$, $CO_2$ or $NO_2$ reference gas, depending on the solid electrolyte 14 and 16 used. The amount of $SO_2$, $CO_2$ or $NO_2$ generated by equilibrium dissociation of the second solid electrolyte 14 and 16 will be on the order of 0.5 ppm (parts per million) to 100 ppm, whereas the amount of $SO_2$, $CO_2$ or $NO_2$ in the monitored gas environment may be from 50 ppm to 2500 ppm, in most cases. There is no separate, exterior reference gas stream associated with this sensor apparatus. The only useful cations in the second solid electrolyte 14 and 16 are $K^+$ and $Na^+$, as they provide the best combination of low electrolyte resistance and highest decomposition temperature for the anions used.

Ideally, the partial pressure of $SO_2$ and $O_2$ or the other dissociation gas species at the reference electrode means 15, would be equivalent to the true dissociation pressure of $K_2SO_4$, or the other useful solid electrolytes described hereinbefore, at a controlled temperature, if the reference electrode is perfectly sealed in the second solid electrolyte section 16 without formation of any minute voids. Presence of minute voids in solid electrolyte section 16 could trap a variety of gas species during the electrolyte fabrication process, and could also accumulate $SO_2$ and $O_2$ gases from the dissociation reaction of solid electrolyte during sensor cell operation. The preferred solid electrolyte section 16 in this invention will be substantially free of minute voids. It will preferably be at least from 95% dense. Solid electrolyte sections 14 and 16 and electrolyte vessel 11 will preferably be at least 98% dense.

Since any voids present in the solid electrolyte section 16 would be minute under presently used powder sintering techniques, and they would be either hermetically sealed or confined in a small space, these trapped gas species would tend to be in equilibrium with the solid electrolyte at a controlled temperature. Therefore, a stable and constant partial pressure of $SO_2 + O_2$, or $CO_2 + O_2$, or $NO_2 + O_2$ is expected to be maintained at the reference electrode means 15, which would result in a stable and reproducible EMF measurement. What is essential is to establish a constant partial pressure of $SO_2 + O_2$, or $CO_2 + O_2$, or $NO_2 + O_2$ at the reference electrode means 15 during sensor cell operation.

The dual gas sensor cell can be made by providing a high density, gas impermeable cylindrical cup of high purity, stabilized zirconia, to act as a first solid electrolyte in the form of a containment vessel. A small hole can be drilled at the closed end, a platinum reference electrode disc positioned inside the cup at the closed end, and a platinum lead wire inserted through the hole and soldered to the electrode. High temperature ceramic sealant can be used over the drilled hole on the outside of the zirconia cup. Then, a fine powder of potassium or sodium sulfate, or potassium or sodium carbonate, or potassium or sodium nitrate second electrolyte material can be packed into the zirconia cup, and against the reference electrode.

This alkali salt electrolyte powder would then be press-sintered at a temperature about 100° C. below its melting point. Melting points are 1072° C. for potassium sulfate, 891° C. for potassium carbonate, and 337° C. for potassium nitrate. This will provide an essentially void free, gas impermeable, solid electrolyte, preferably with no cracking upon cooling. Then, a specially densified, outer second electrolyte section, of the same material as the inside electrolyte section can be pressed into place and sintered, or held with ceramic adhesive or a pressure or spring means.

A first platinum monitor electrode can then be placed on top of the densified, second solid electrolyte section across the top of the enclosing cup, and platinum lead wire soldered in place. Finally, a platinum wire coil can be wound around the zirconia cup bottom to provide a second monitor electrode means. The leads can then be connected to gas-monitoring circuitry, usually including two voltmeters, and the gas sensor cell placed in a monitoring gas environment, usually in an encasing probe means with a heater and heater controls and operated at an operating temperature effective to cause equilibrium dissociation of the second solid electrolyte. i.e., the sulfate, carbonate, or nitrate materials. The sensor must be operated at a temperature substantially below the melting point of either of the solid electrolytes.

The invention will now be illustrated by the following example.

EXAMPLE

A double cell, self-generating referencing, combined, dual gas sensor, similar to that shown in FIG. 1, was made. A high purity (99+%) yttria doped zirconia $(ZrO_2)_{0.9}(Y_2O_3)_{0.1}$, closed end tube, approximately 1.5 cm long, 1.1 cm outside diameter, and 0.2 cm thick, isostatically pressed to 98% density, was drilled at the middle of the closed end to provide a small hole about 1 mm. in diameter. This provided a first electrolyte in the form of a container vessel. Platinum wire was inserted through the hole, would as a support, and soldered to a platinum electrode screen having a diameter of approximately 0.8 cm, held in place against the bottom of the tube. Powdered, 99% pure $K_2SO_4$, having a submicron particle size, was poured into the bottom of the tube, on top of the electrode to a bit over the top of the tube and tamped in place. The wire was sealed as in FIG. 1 at point 21, by a mixture of 49 mole % $La_2O_3$ and 51 mole % $Al_2O_3$.

The $K_2SO_4$ filled tube was then hot pressed with a plunger at approximately 980° C. This caused the $K_2SO_4$ particles to come into very intimate contact, and to heat-sinter together, to form an essentially void-free, 98% dense, solid, second electrolyte section. A specially densified disc, about 99% dense, of 99% pure $K_2SO_4$ was then pressed and sintered onto the end of the zirconia vessel into intimate contact with the in-place section of $K_2SO_4$ electrolyte. A first, exterior, platinum monitor electrode screen was then pressed and bonded to the top of the outer $K_2SO_4$ densified electrolyte disc. A second, exterior, platinum monitor electrode, in the form of contacting would wire, was wrapped around the bottom of the zirconia vessel. Platinum wire was then attached to the monitor electrodes. Wire leads from the two monitor electrodes and encapsulated interior sensing electrode were connected to two Keithley digital voltmeters in the circuit shown in FIG. 1. The whole sensor was assembled into a probe structure having a heating element and temperature control to provide a gas sensor apparatus.

The dual gas sensor apparatus was placed in a monitored gas environment containing $SO_2$ and $O_2$ gases, at 850° C., and EMF values were measured. Table 1 shows the results of the $K_2SO_4$ electrolyte cell and the stabilized zirconia electrolyte cell:

TABLE 1

| Sample | Gas Mixture | EMF in mV. of $O_2$ cell | EMF in mV. of $SO_2$ cell |
|---|---|---|---|
| 1 | 5000 ppm $SO_2$ in Air | −236 | −6 |
| 2 | 5000 ppm $SO_2$ in Air | −238 | −5 |
| 3 | 5000 ppm $SO_2$ in Air | −233 | −6 |
| 4 | 5000 ppm $SO_2$ in Air | −233 | −6 |
| 5 | 110 ppm $SO_2$ in 1% $O_2$, rest $N_2$ | 41 | 71 |
| 6 | 110 ppm $SO_2$ in 1% $O_2$, rest $N_2$ | 43 | 71 |
| 7 | 110 ppm $SO_2$ in 1% $O_2$, rest $N_2$ | 40 | 70 |
| 8 | 1% $SO_2$ in 1% $O_2$, rest $N_2$ | −151 | 71 |
| 9 | 1% $SO_2$ in 1% $O_2$, rest $N_2$ | −148 | 71 |
| 10 | Air i.e. 21% $O_2$, rest $N_2$ | 110 | −6 |
| 11 | 0.2% $O_2$ in $N_2$ | 254 | 103 |

Figure 2:
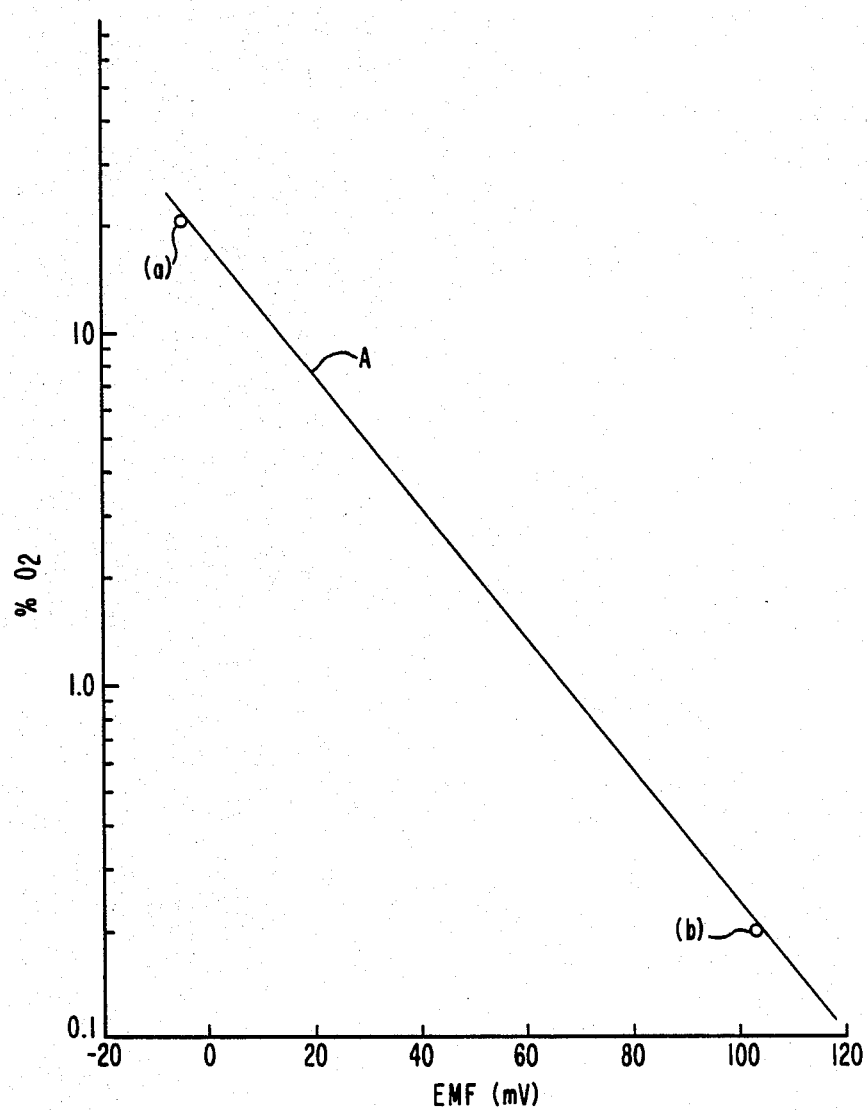
FIG. 2 shows an $O_2$ calibration curve at 850° C., of EMF vs. % $O_2$, for the dual reference gas sensor of this invention.

The $O_2$ calibration, Curve A, of the stabilized zirconia cell in the sensor is shown in FIG. 2, taken from Sample 10 and 11 data, as points (a)=−6 and (b)=103 respectively. The slope of Curve A is about 54 mV per decade of $O_2$ concentration. The term "decade" concentration means, for example, on a log scale, 1 ppm to 10 ppm, or 10 ppm to 100 ppm, or 100 ppm to 1,000 ppm, etc., as shown in FIGS. 2 and 3

Figure 3:
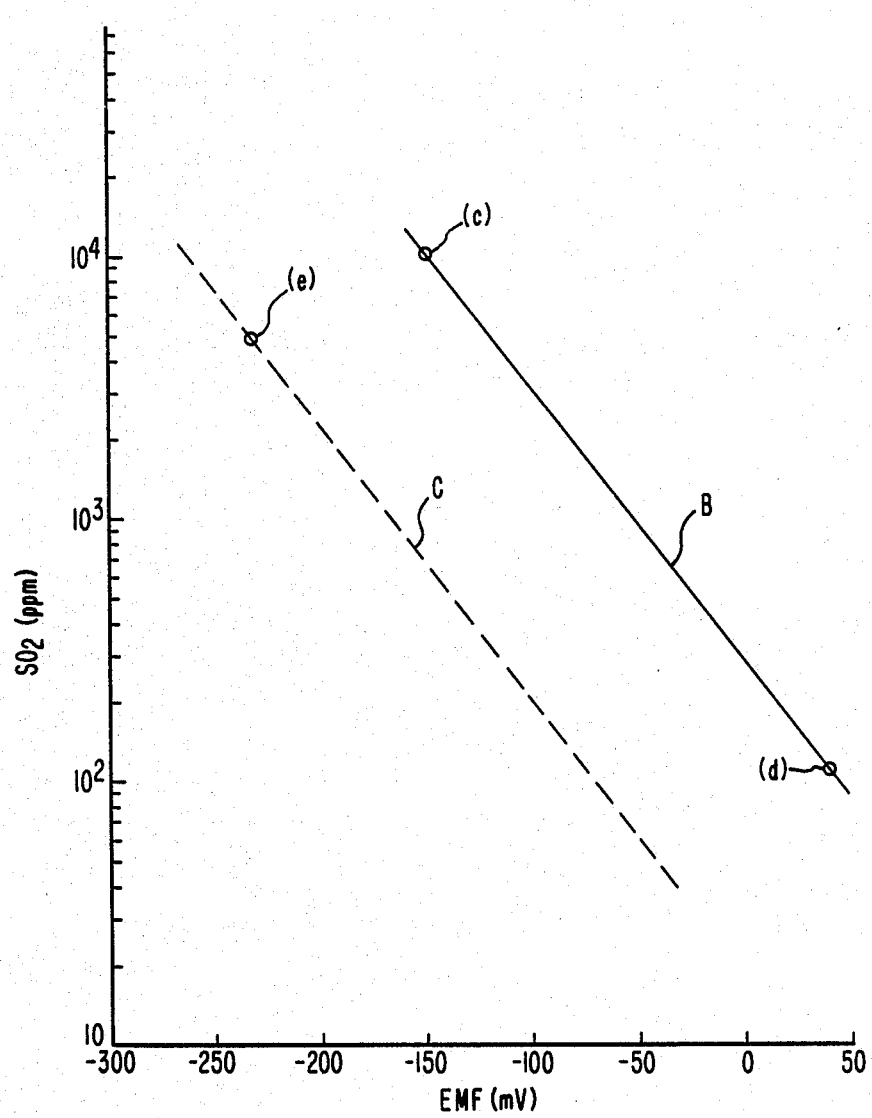
FIG. 3 shows $SO_2+O_2$ calibration curves at 850° C., of EMF vs. ppm $SO_2$, for the dual reference gas sensor of this invention.

The $SO_2+O_2$ calibration curves of the $K_2SO_4$ cell in the sensor are shown in FIG. 3, taken from Sample 1 to 9 data. Curve B shows a −150 mV reading from 10,000 ppm $SO_2$ (1% $SO_2$) in 1% $O_2$ with the balance $N_2$, point (c) from Samples 8 and 9 and a 40 mV reading for 110 ppm $SO_2$ in 1% $O_2$, with the balance $N_2$, point (d) from Samples 5 to 7. Curve B has a slope of 95 mV per decade of $SO_2$ concentration. Point (e), from Samples 1 to 4, shows a reading for 5,000 ppm $SO_2$ in air, i.e., in 21% $O_2$ with the rest $N_2$. Only one experimental point was calibrated, but knowing the slope of $SO_2$ as 95 mV. per decade of $SO_2$ concentration (Curve B), Curve C was deduced for 5000 ppm $SO_2$ in air.

These test results revealed that both the zirconia cell and the $K_2SO_4$ cell of the sensor responded to $O_2$ and to $SO_2+O_2$ fairly well in agreement with the prediction of the Nernst equations. As shown in Table 1, the reproducibility of the sensor apparatus to different $SO_2$ and $O_2$ levels was very good.

Since the partial pressure of total reference gas, i.e., $SO_2$ and $O_2$, at the surface of the reference electrode is determined by the dissociation pressure of $K_2SO_4$ and the equilibrium pressure of entrapped gas and $K_2SO_4$, it is essential to maintain a fairly constant cell temperature and a gas leak-free region between the reference electrode and the environment for successful operation of this integral cell.

This sensor apparatus presents a simple and practical combined $SO_2/O_2$ sensor unit to monitor $SO_2$ and $O_2$ levels in flue gases.

We claim:

1. A solid electrolyte dual gas sensor for measuring two selected component gases of a monitored gas environment by generating electrical signals on the basis of a difference in the partial pressure between (a) the two selected component gases of the monitored gas environment at first and second monitor electrodes in contact with the monitored gas environment and solid electrolyte, and (b) corresponding component reference gases at reference electrode means in contact with a reference gas environment and solid electrolyte comprising a single reference electrode surrounded by a first solid electrolyte and a separate second solid electrolyte and being isolated from the monitored gas environment, said reference electrode contacting both said electrolytes, said first electrolyte being oxygen ion conductive and said second electrolyte having a single component composition conductive to sodium or potassium ions, one monitor electrode contacting the first solid electrolyte and the other monitor electrode contacting the second solid electrolyte, said second electrolyte being adapted upon heating to dissociate and provide the sole source of constant partial pressures of reference gases at the reference electrode corresponding to the selected component gases to be measured in the monitored gas environment, to provide a unitary, dual gas sensor.

2. The solid electrolyte dual gas sensor of claim 1, wherein the second solid electrolyte is divided into an inside section in physical contact with an outside section, said outside electrolyte section being in contact with the monitored gas environment and acting to prevent contact of the monitored gas environment with the reference electrode, and wherein the reference electrode is of platinum.

3. The solid electrolyte dual gas sensor of claim 1, wherein the reference and monitor electrodes are metal electrodes that are attached to circuit means which are effective to generate an electrical signal measurement of the selected gas components in the monitored gas environment.

4. The solid electrolyte dual gas sensor of claim 3, wherein a first electrical circuit connects the reference electrode to the monitor electrode in contact with the second solid electrolyte, and a second electrical circuit connects the reference electrode to the monitor electrode in contact with the first solid electrolyte and wherein the second circuit contains circuit shorting means.

5. The solid electrolyte dual gas sensor of claim 1, wherein the first solid electrolyte comprises zirconia and the second solid electrolyte is selected from one of the group consisting of $K_2SO_4$, $Na_2SO_4$, $K_2CO_3$, $Na_2CO_3$, $KNO_3$ and $NaNO_3$.

6. The solid electrolyte dual gas sensor of claim 1, wherein a stable and constant partial pressure of the self-generated gases are maintained at the reference electrode.

7. The solid electrolyte dual gas sensor of claim 1, wherein the second solid electrolyte is selected from one of the group consisting of $K_2SO_4$ and $Na_2SO_4$, and the selected gas components present in the monitored gas environment are $SO_2$ and $O_2$.

8. The solid electrolyte dual gas sensor of claim 1, wherein the first electrolyte provides a container for the reference electrode.

9. A solid electrolyte dual gas sensor comprising: a container comprising zirconia solid electrolyte in contact with a metal monitor electrode exposed to a monitored gas environment containing selected gas components to be measured, a single platinum reference electrode disposed within said container and contacting both the zirconia electrolyte and a separate, second, solid electrolyte, said platinum reference electrode being isolated from the monitored gas environment by the zirconia electrolyte and the second solid electrolyte, said second electrolyte having a single component composition selected from one of the group consisting of $K_2SO_4$, $Na_2SO_4$, $K_2CO_3$, $Na_2CO_3$, $KNO_3$ and $NaNO_3$ and contacting a second metal monitor electrode exposed to the monitored gas environment, said second solid electrolyte being adapted to dissociate and provide the sole source of reference gases at the reference electrode, corresponding to the selected gas components to be measured in the monitored gas environment.

10. The solid electrolyte dual gas sensor claim 9, wherein the second solid electrolyte is selected from one of the group consisting of $K_2SO_4$ and $Na_2SO_4$, and the selected gas components present in the monitored gas environment are $SO_2$ and $O_2$.

11. The solid electrolyte dual gas sensor of claim 9, wherein the second solid electrolyte is divided into an inside section in physical contact with an outside section, said outside electrolyte section being in contact with the monitored gas environment and acting to prevent contact of the monitored gas environment with the reference electrode, and wherein the second metal monitor electrode contacts the outside electrolyte section.

12. The solid electrolyte dual gas sensor of claim 9, wherein the reference and monitor electrodes are metal electrodes that are attached to circuit means which are effective to generate an electrical signal measurement of the selected gas components in the monitored gas environment.

13. The solid electrolyte dual gas sensor of claim 12, wherein a first electrical circuit connects the reference electrode to the monitor electrode in contact with the second solid electrolyte, and a second electrical circuit connects the reference electrode to the monitor electrode in contact with the zirconia solid electrolyte and wherein the second circuit contains circuit shorting means.

* * * * *